US012788817B2

(12) United States Patent
Stamplecoskie et al.

(10) Patent No.: US 12,788,817 B2
(45) Date of Patent: Nov. 10, 2026

(54) PEPTIDE-PROTECTED GOLD NANOCLUSTER AND USE IN PHOTODYNAMIC THERAPY

(71) Applicants: Queen's University at Kingston, Kingston (CA); University Health Network, Toronto (CA)

(72) Inventors: Kevin Stamplecoskie, Kingston (CA); Parimah Aminfar, Kingston (CA); Goonay Yousefalizadeh, Aurora (CA); Gang Zheng, Toronto (CA); Juan Chen, Toronto (CA)

(73) Assignees: Queen's University at Kingston, Kingston (CA); University Health Network, Toronto (CA)

( * ) Notice: Subject to any disclaimer, the term of this patent is extended or adjusted under 35 U.S.C. 154(b) by 333 days.

(21) Appl. No.: 18/736,918

(22) Filed: Jun. 7, 2024

(65) Prior Publication Data

US 2024/0408209 A1 Dec. 12, 2024

Related U.S. Application Data

(60) Provisional application No. 63/471,672, filed on Jun. 7, 2023.

(51) Int. Cl.
*A61K 33/242* (2019.01)
*A61K 41/00* (2020.01)
*A61N 5/06* (2006.01)

(52) U.S. Cl.
CPC ........ *A61K 41/0023* (2013.01); *A61K 33/242* (2019.01); *A61N 5/062* (2013.01)

(58) Field of Classification Search
CPC ... A61K 41/0023; A61K 33/242; A61N 5/062
See application file for complete search history.

(56) References Cited

U.S. PATENT DOCUMENTS 8,790,934 B2 7/2014 Penades et al.
9,090,660 B2 7/2015 Gao

FOREIGN PATENT DOCUMENTS

EP 1977754 A1 10/2008

OTHER PUBLICATIONS

Le et al, STIC Translation (Year: 2018).*
Le et al (Year: 2018).*
Aminfar et al (Year: 2023).*
Sych, T. S., et al., "Fluorescent Silver Clusters on Protein Templates: Understanding Their Structure", The Journal of Physical Chemistry C 2018, 122 (51), 29549-29558.
Tang, L., et al., "Theranostic Gold Nanoclusters for NIR-II Imaging and Photodynamic Therapy", Chemical Research in Chinese Universities 2021, 37 (4), 934-942.
Zhang, Y., et al., "Ultrasmall Au nanoclusters for biomedical and biosensing applications: A mini-review", Talanta 2019, 200, 432-442.
Ramsay, H. S., et al., "Light activated synthesis of the atomically precise fluorescent silver cluster Ag18(Capt) 14", Nanoscale 2019, 11 (43), 20522-20526.
Stamplecoskie, K. G., et al., "Excited-State Behavior of Luminescent Glut tected Gold Clusters", The Journal of Physical Chemistry C 2014, 118 (2), 1370-1376.
Yousefalizadeh, G.; et al., "Norrish type I photochemistry as a powerful tool in the isolation of thiol protected Au25SR18 clusters", Journal of Photochemistry and Photobiology A: Chemistry 2018, 353, 251-254.22.
Conway, C. L., et al., "In vivo and in vitro characterisation of a protoporphyrin IX-cyclic RGD peptide conjugate for use in photodynamic therapy", Photochem Photobiol Sci 2008, 7 (3). 290-8.
Kawasaki, H., et al., "Generation of Singlet Oxygen by Photoexcited Au25(SR)18 Clusters", Chemistry of Materials 2014, 26 (9), 2777-2788.
Yin, Y., et al., "RGDC Functionalized Titanium Dioxide Nanoparticles induce Less Damage to Plasmid DNA but Higher Cytotoxicity to HeLa Cells", The Journal of Physical Chemistry B 2013, 117 (1), 125-131.
He, L., et al., "A highly selective dual-therapeutic nanosystem for simultaneous anticancer and antiangiogenesis therapy", Journal of Materials Chemistry B 2017, 5 (41), 8228-8237.
Wan, Z., et al., "NIR light-assisted phototherapies for bone-related diseases and bone tissue regeneration: A systematic review", Theranostics 2020, 10 (25), 11837-11861.
Li, R., et al., "Asymmetric, amphiphilic RGD conjugated phthalocyanine for targeted photodynamic therapy of triple negative breast cancer", Signal Transduction and Targeted Therapy 2022, 7 (1), 64.
Li, X., et al., "The Peptide Functionalized Inorganic Nanoparticles for Cancer-Related Bioanalytical and Biomedical Applications", Molecules, 2021, 26, 3228.

(Continued)

*Primary Examiner* — Jeffrey S Lundgren
*Assistant Examiner* — Ibrahim D Bori
(74) *Attorney, Agent, or Firm* — Stephen J. Scribner

(57) ABSTRACT

A gold nanocluster of the formula $Au_{16}(RGDC)_{14}$, wherein RGDC is arginine-glycine-aspartic acid-cysteine, and methods for synthesis, are described. The gold nanocluster effectively produces Type I ROS and functions as photosensitizer, and has utility in applications such as, but not limited to, biomedical applications and photocatalysis. The gold nanocluster may be useful in photodynamic therapy (PDT) in cells and tissues for treating diseases such as certain cancers.

12 Claims, 10 Drawing Sheets

(56) References Cited

OTHER PUBLICATIONS

Dayan, A., et al., "RGD-modified dihydrolipoarnide dehydrogenase conjugated to titanium dioxide nanoparticles—switchable integrin-targeted photodynamic treatment of melanoma cells† ", RSC Adv., 2018, 8, 9112-9119.

Cruje, C., et al., "Optimization of PEG Coated Nanoscale Gold Particles for Enhanced Radiation Therapy", RSC Adv., 2015. 00, 1-3.

Sun, W., et al., Aggregation-Induced Emission Gold Clustoluminogens for Enhanced Low-Dose X-ray-Induced Photodynamic Therapy:, Angew. Chem. Int. Ed. 2020, 59, 9914-9921.

* cited by examiner

PEPTIDE-PROTECTED GOLD NANOCLUSTER AND USE IN PHOTODYNAMIC THERAPY

RELATED APPLICATION

This application claims the benefit of the filing date of Application No. 63/471,672, filed Jun. 7, 2023, the contents of which are incorporated herein by reference in their entirety.

BACKGROUND

The synthesis and isolation of atomically precise gold and silver clusters has recently attracted an increase in research interest [1-3]. This is especially true for water soluble clusters, intended for biomedical imaging and therapy. However, aqueous clusters typically are more challenging to isolate in high purity, and are extremely challenging to crystallise for structural characterization [4-6]. Among them, peptide-protected gold nanoclusters (AuNCs) have been of particular interest for their good biocompatibility, and biological activity conferred by the ligand [4, 5]. Like other aqueous clusters, they are often difficult to characterize by mass spectrometry due to their propensity of fragmentation into complex isotope patterns [4].

Owing to their long-lived excited state, clusters have been of particular interest as photocatalysts and for their use as photosensitizers in photodynamic therapy (PDT). For example, glutathione-protected Au clusters have been shown to be effective $^1O_2$ photosensitizers, which has been attributed to their reactive excited-state [7]. Type I and Type II are used to denote two pathways to different reactive oxygen species (ROS), radicals formed from electron transfer from the excited-state (Type I, can include other electron transfer reactions) and singlet oxygen formed by excited-state energy transfer (Type II). Most PDT studies on clusters have focussed investigations on Type II ROS production ($^1O_2$ generation). Type I ROS generation of clusters has unique advantages, such as the ability to generate reactive radicals with other substrates than oxygen, and has been under explored for nanoclusters. Furthermore, before clinical use is possible, it is important to determine not only the effect of clusters in photodynamic therapy but the effect of the in vitro environment on clusters, and to track their fate in the body.

Typical synthesis of AuNCs often leads to a distribution of sizes with various numbers of metal atoms and ligands. Importantly, these variations lead to significant differences in excited-state properties. Typical characterization methods of nanoclusters such as absorbance, emission, and mass spectrometry are of value in identifying cluster molecular formulae, but have their limitations (e.g., many cluster species do not survive harsh ionizing conditions in mass spectrometry, resulting in fewer species identified than what is present in samples before injection).

SUMMARY

According to one aspect of the invention there is provided a gold nanocluster of the formula $Au_{16}(RGDC)_{14}$, wherein RGDC is arginine-glycine-aspartic acid-cysteine.

According to another aspect of the invention there is provided a method for providing photodynamic therapy to a subject, comprising: providing $Au_{16}(RGDC)_{14}$ nanoclusters to the subject, wherein cells of the subject uptake the nanoclusters; and subjecting the cells to irradiation with light; wherein cell death is induced in at least a portion of the cells that uptake the $Au_{16}(RGDC)_{14}$ nanoclusters.

In one embodiment at least a portion of the cells wherein cell death is induced are cancer cells.

In one embodiment the $Au_{16}(RGDC)_{14}$ nanoclusters are provided to the subject at a concentration up to about 500 μg/mL.

In one embodiment the cells are subjected to irradiation with visible light.

In one embodiment subjecting the cells to irradiation with light causes Type I ROS generation by the $Au_{16}(RGDC)_{14}$ nanoclusters in the cells.

According to another aspect of the invention there is provided a method for treating cancer, comprising: providing $Au_{16}(RGDC)_{14}$ nanoclusters to cancer cells, wherein at least a portion of the cancer cells uptake the nanoclusters; and subjecting the cancer cells to irradiation with light; wherein cell death is induced in at least a portion of the cancer cells that uptake the $Au_{16}(RGDC)_{14}$ nanoclusters.

According to another aspect of the invention there is provided method for synthesizing a gold nanocluster of the formula $Au_{16}(RGDC)_{14}$, wherein RGDC is arginine-glycine-aspartic acid-cysteine, according to embodiments described herein with optimized reaction conditions including an optimized concentration of a reducing agent and an optimized pH.

In one embodiment a method for synthesizing a gold nanocluster of the formula Au16(RGDC)14 comprises reducing Au(III) to Au(I) at a pH of about 10 using excess thiol ligand to obtain a thiol coordinated intermediate Au(I)x(SR)x; reacting the Au(I)x(SR)x with a photochemical initiator using UVA irradiation at about 360 nm to obtain alpha-hydroxy radicals; obtaining a product emitting at about 770 nm; and purifying the Au16(RGDC)14 in the product by centrifuging to remove unwanted photoproducts.

In one embodiment the concentration of the Au(III) is at least 3 mM.

In one embodiment the photochemical initiator comprises Omnirad® 2959.

In one embodiment the Omnirad® 2959 concentration is about 3 mM.

One embodiment comprises centrifuging using centrifugal filters with a cut-off of about 3 kDa.

One embodiment comprises centrifuging to remove unwanted photoproducts emitting at about 420 nm.

One embodiment comprises monitoring absorbance and excitation-emission matrix (EEM) spectra of the product during the irradiating.

One embodiment comprises performing parallel factor (PARAFAC) analysis on EEM spectra to determine emissive components and their relative contributions to the emission of the product.

One embodiment comprises removing Rayleigh scattering from each EEM spectra prior to PARAFAC analysis.

One embodiment comprises determining a score value of at least one component of a model of the product for successive EEM spectra, determining a plateau of the score value of the at least one component, and stopping the reaction by stopping the UVA irradiation when the plateau in the score value of the at least one component is reached.

BRIEF DESCRIPTION OF THE DRAWINGS

For a greater understanding of the invention, and to show more clearly how it may be carried into effect, embodiments will be described, by way of example, with reference to the accompanying drawings, wherein.

DETAILED DESCRIPTION OF EMBODIMENTS

Figure 1:
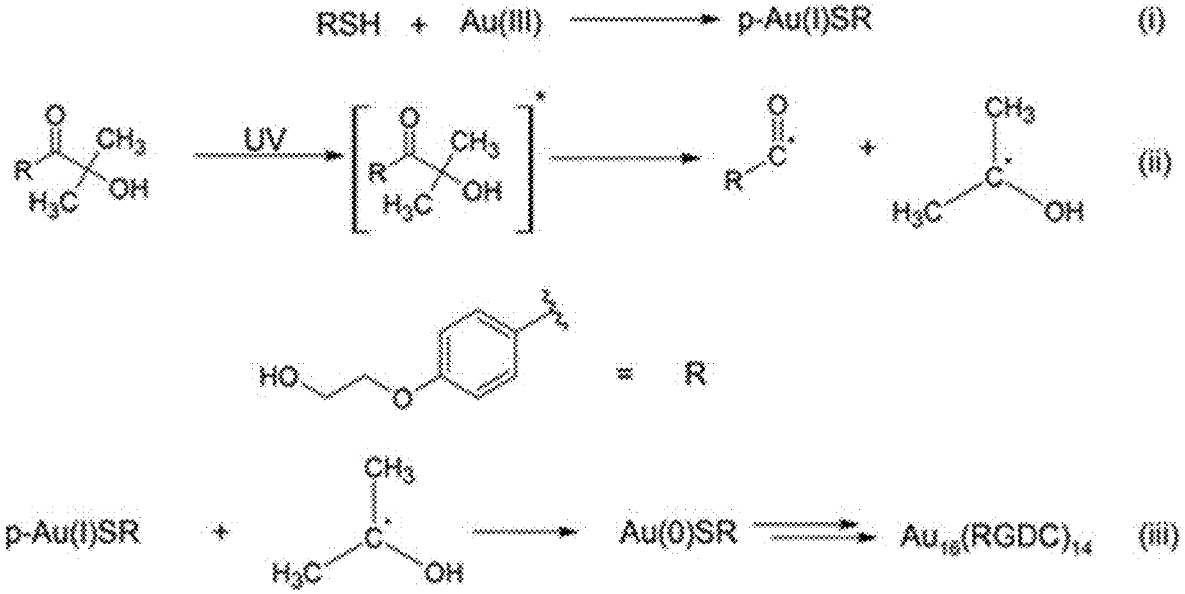
FIG. 1 shows a scheme for synthesis of $Au_{16}(RGDC)_{14}$ using Omnirad® 2959 as a photochemical initiator, according to one embodiment.

Synthesis of metal clusters most commonly uses reducing agents like $NaBH_4$, where the controlled reduction presents a challenge, and a mixture of clusters often results. As described herein, using a Norrish Type I reaction, alpha-hydroxy radicals were generated as a reducing agent from a photochemical initiator (e.g., Omnirad® 2959), wherein a convenient control over the most challenging aspects of metal cluster synthesis is provided (FIG. 1). In this light-activated method the concentration of radicals can be regulated by controlling the ultraviolet A (UVA) intensity. As described herein, the Norrish Type I reaction conditions were specifically optimized for producing emissive $Au_{16}(RGDC)_{14}$ clusters, which included optimizing the concentration of the reducing agent and optimizing the pH of the solution. RGDC is a thiol containing peptide with the sequence arginine-glycine-aspartic acid-cysteine that has previously been attached to photosensitizers in (PDT) for enhanced accumulation in tumour cells [8-12]. However, a single purified gold nanocluster ligated with RGDC has not been previously produced.

As used herein, the terms "cluster" and "nanocluster" are used interchangeably and refer to atomically precise structures in a size range smaller than nanoparticles (e.g., typically up to about 2 nm). Unlike metal nanoparticles, metal nanoclusters have well-defined molecular orbitals with discrete energy transitions and size-dependent excited-state properties. Metal nanoclusters can be characterized by molecular techniques such as single crystal X-ray diffraction, nuclear magnetic resonance spectroscopy, and mass spectrometry. Unlike nanoparticles, which are a conglomeration of materials with an average size distribution and show surface plasmon resonance (SPR), nanoclusters are made of an exact number of metal atoms and organic ligands, e.g., thiols, phosphines, and halides. Due to their small sizes, they show molecular-like features, including distinct electronic transitions and photoluminescence, which are not observed for their bigger counterparts.

Fluorescence excitation-emission matrix (EEM) spectroscopy with parallel factor (PARAFAC) analysis was used as a non-destructive, in-situ technique to assess the number of emissive clusters in a sample and to verify the optical purity of the $Au_{16}(RGDC)_{14}$ clusters. The assignment of $Au_{16}(RGDC)_{14}$ was supported by high resolution Electrospray Ionization Mass Spectrometry (ESI-MS).

Briefly, synthesis of $Au_{16}(RGDC)_{14}$ clusters was carried out by adding a 9 mM aqueous solution of RGDC to an aqueous solution of $HAuCl_4$ (3 mM). 3 mM aqueous solution of Omnirad 2959 was subsequently added to the reaction vial. The pH of the reaction solution was then adjusted to 10 using minimum amount of 1 M $NaOH_{(aq)}$. The solution was then transferred to quartz cuvettes and purged with $N_2$ for 15 minutes to remove oxygen. 5 UVA lamps (250 $Wm^{-2}$) were used to irradiate the reaction solution for 30 minutes. The absorbance and emission of the product were monitored during the irradiation. The AuNCs were concentrated and purified by centrifugation, using centrifugal filters with a 3 kDa cut-off. The samples were stored in a refrigerator and were stable for more than a month at 4° C.

Figure 2:
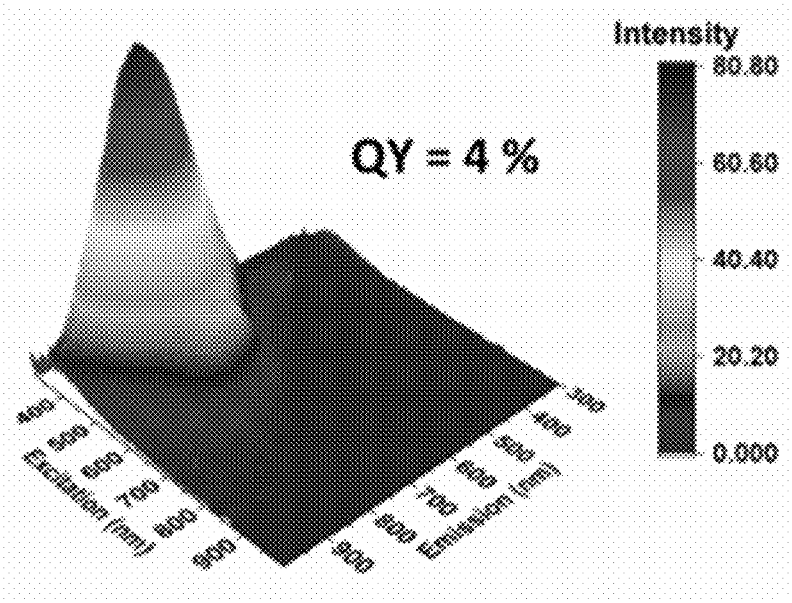
FIG. 2 is a fluorescence excitation-emission matrix (EEM) spectroscopy plot of purified nanoclusters.

The first step (FIG. 1, (i)) of the synthesis of $Au_{16}(RGDC)_{14}$ involved reducing Au(III) to Au(I) using excess thiol ligand, forming the thiol coordinated intermediate $Au(I)_x(SR)_x$. The second step (FIG. 1, (ii) and (iii)) was initiated by the formation of alpha-hydroxy radicals upon UVA irradiation (360 nm). The radicals were produced through a Norrish type I cleavage with a quantum yield of formation of 0.29. After 30 minutes of irradiation, clusters emitting at 770 nm were obtained. During the synthesis, the emission of the product was monitored using fluorescence EEM (FIG. 2). There is a 420 nm emission, indicative of photoproducts of Omnirad 2959, which was removed upon centrifugation.

Figure 3A:
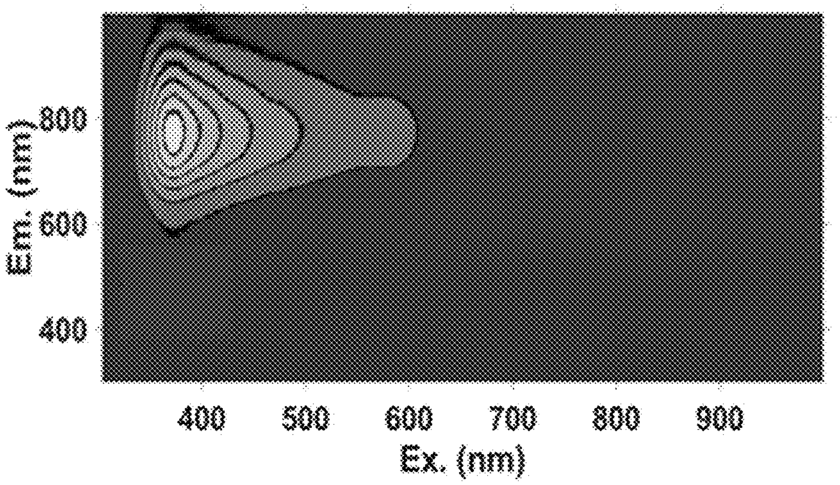
FIG. 3A is a plot of EEM spectrum of $Au_{16}(RGDC)_{14}$ nanoclusters from the PARAFAC.
Figure 3B:
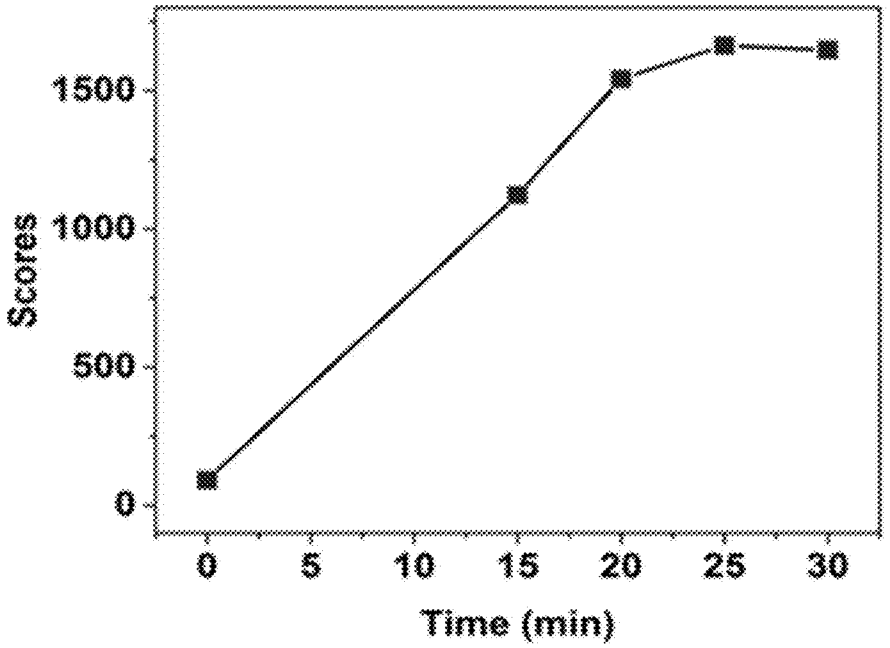
FIG. 3B is a score plot of the 1-component model calculated using the drEEM toolbox for MATLAB, where Score is the measure of the amount of the materials at each time point.

PARAFAC analysis was performed on EEM data throughout the synthesis and the number of emissive compounds and relative contribution to the emission in the sample was determined. Before performing PARAFAC analysis, Rayleigh scattering was removed from each EEM spectra of the data set and each EEM was subsequently normalized and smoothed using MATLAB. PARAFAC analysis fits multiple slices of a EEM plot with a common set of factors varying the weight for each slice, determining independent components according to their unique optical properties. An initial guess at the number of the components (in this case 1) that best describe the dataset is used and PARAFAC analysis was then performed on the EEM scans using the drEEM Toolbox for MATLAB (The MathWorks, Inc., Natick, MA, USA) and constraining the component to be non-negative in all dimensions. The EEM plot generated by PARAFAC was found to describe 99.4% of the data, which gave an excellent match with the expected emission profile of the clusters (FIG. 3A). A two-component model was also tested and found to only reproduce noise. Therefore, PARAFAC analysis strongly supported the presence of a single component for the Au clusters. Score values obtained from the model are relative to the concentration of components. The score plot of the 1-component model reached plateau at 25 min, confirming also that the reaction can be stopped by turning off the UV lamps after 25 min when the concentration of the clusters has stopped increasing (FIG. 3B).

To further investigate the purity of the material, native polyacrylamide gel electrophoresis (PAGE) was applied wherein one single band was observed in the gel. The $Au_{16}(RGDC)_{14}$ clusters were found to be quite emissive with the quantum yield of emission of 4% measured by Hamamatsu absolute quantum yield spectrometer.

Figure 4A:
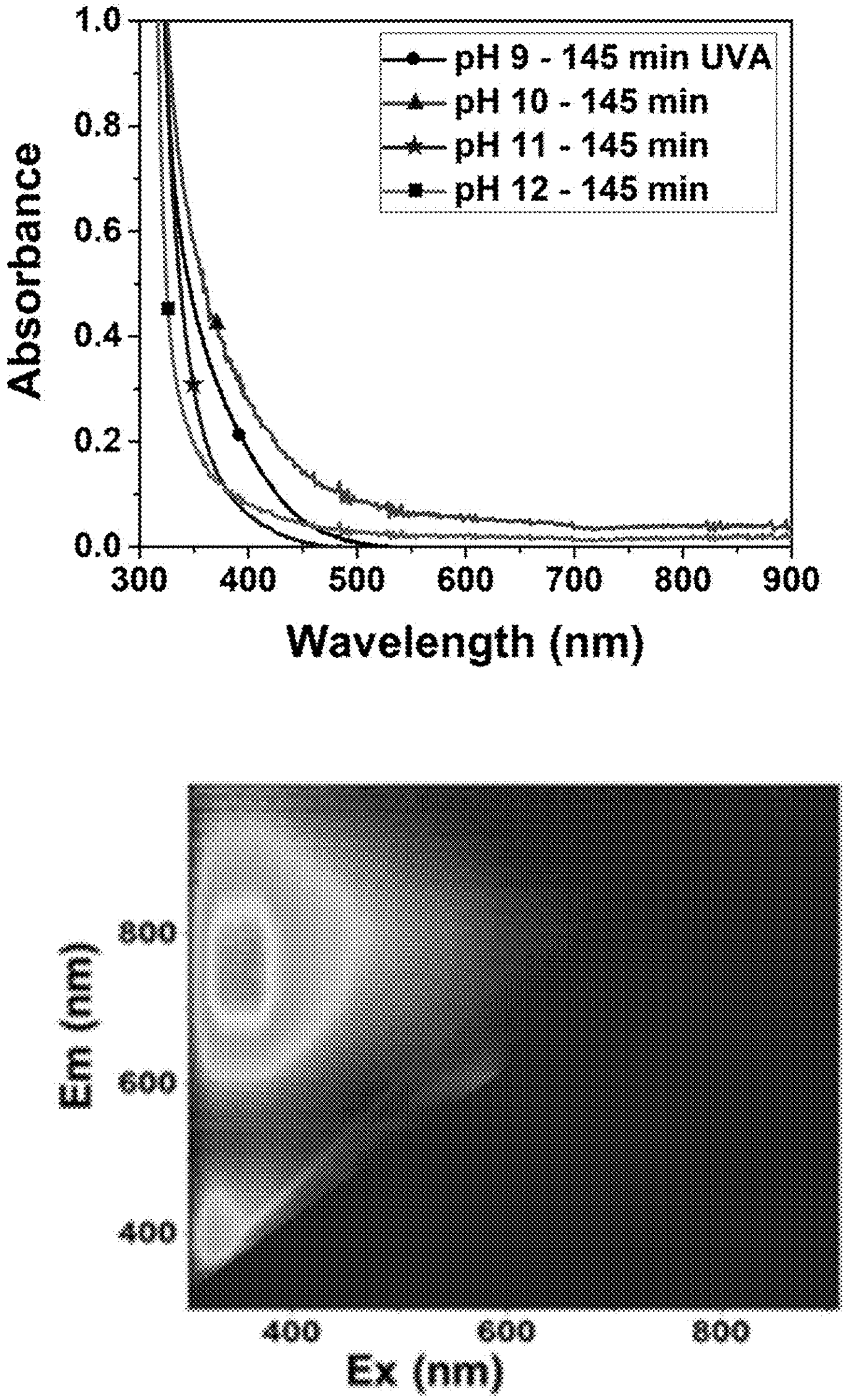
FIGS. 4A-4C are plots of absorbance (upper panels) and emission (lower panels) of Au(RGDC) clusters using 1 mM Au (FIG. 4A), 2 mM Au (FIG. 4B), and 1 mM of Au with 3 mM of Omnirad-2959 (FIG. 4C); EEM plots are shown at pH 10.
Figure 4B:
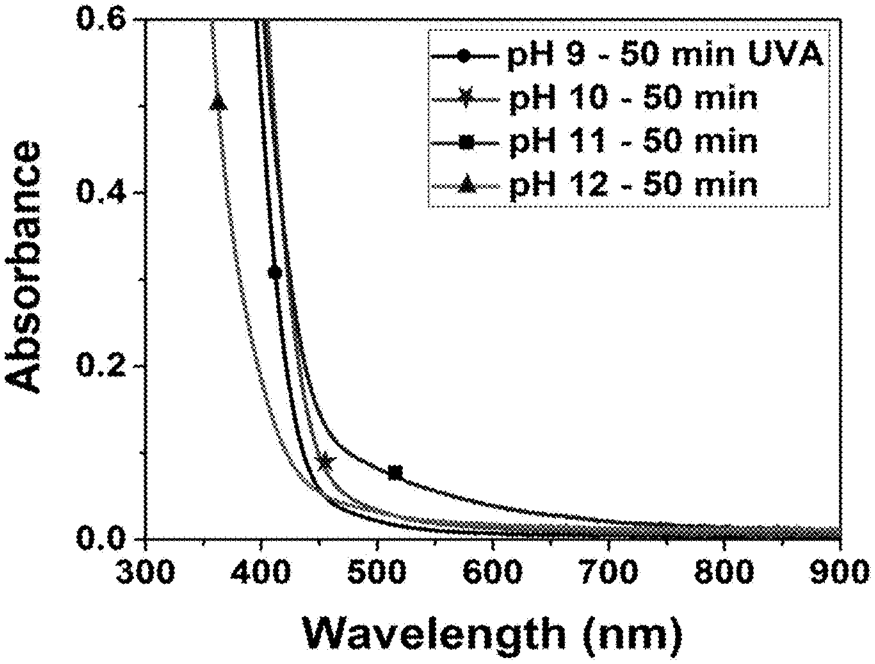
Figure 4B:
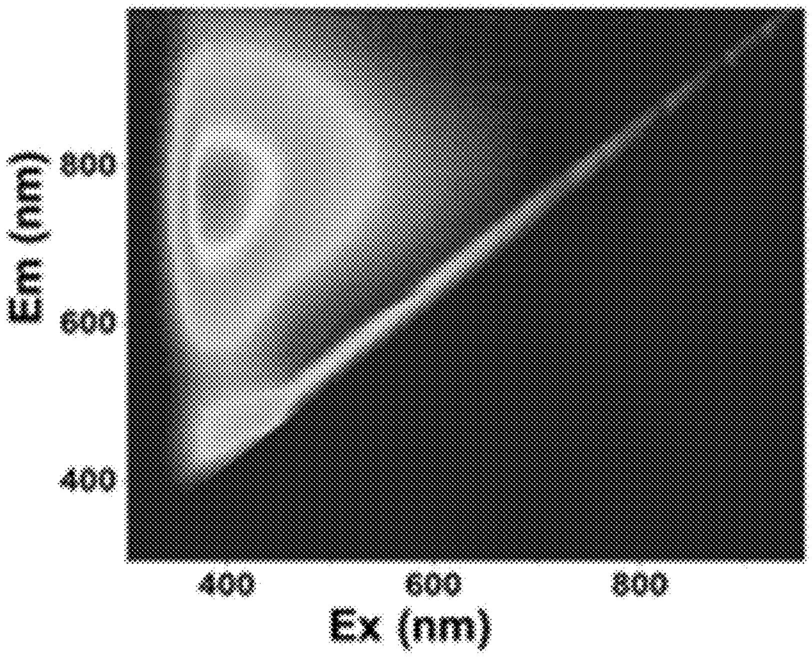
Figure 4C:
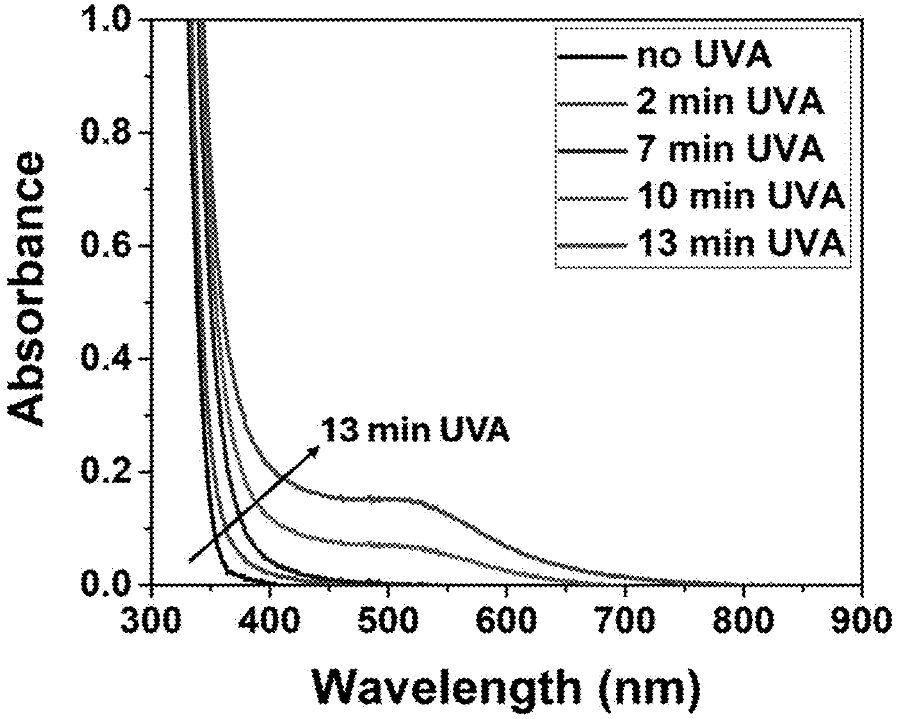
Figure 4C:
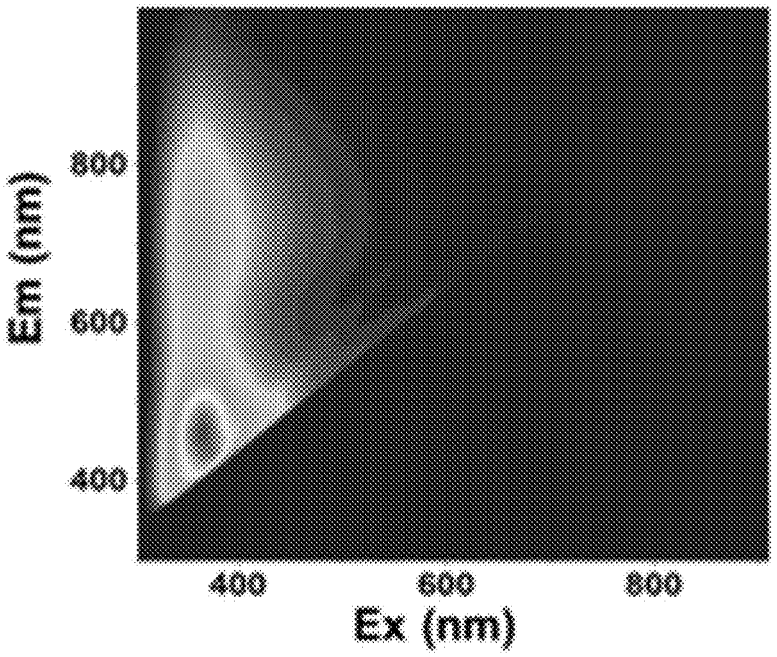

Optimizing the pH of the reaction is an important factor in this synthetic route as the reduction of $Au(I)_x(SR)_x$ intermediates is pH dependent (equation (iii) in the scheme of FIG. 1). For example, the highest reaction yield and the purest sample as assessed by EEM/PARAFAC was obtain for a pH of 10. In addition to the pH, initial concentration of the Au was optimized to obtain the purest product. EEM/PARAFAC showed the presence of more than one emitter when the Au concentration was less than 3 mM (FIGS. 4A and 4B). Excess reducing agent was avoided as it also contributed to mixtures of the clusters and nanoparticles in the solution (FIG. 4C).

Figure 5:
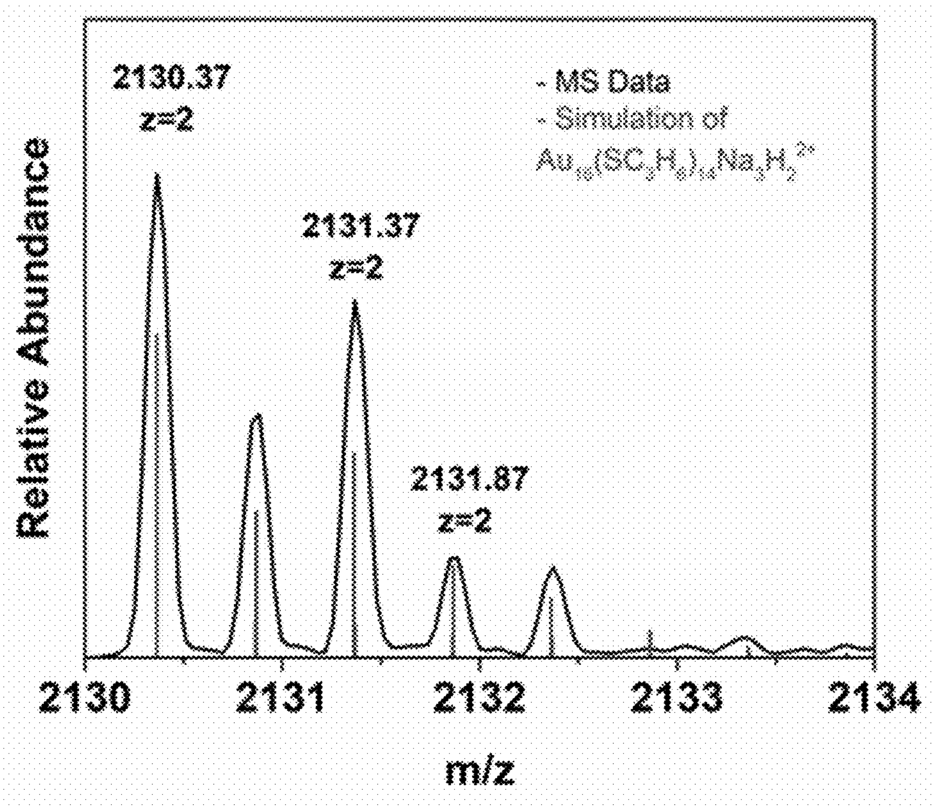
FIG. 5 is a plot of positive ion mode ESI-MS of the $Au_{16}(RGDC)_{14}$ clusters.
Figure 6:
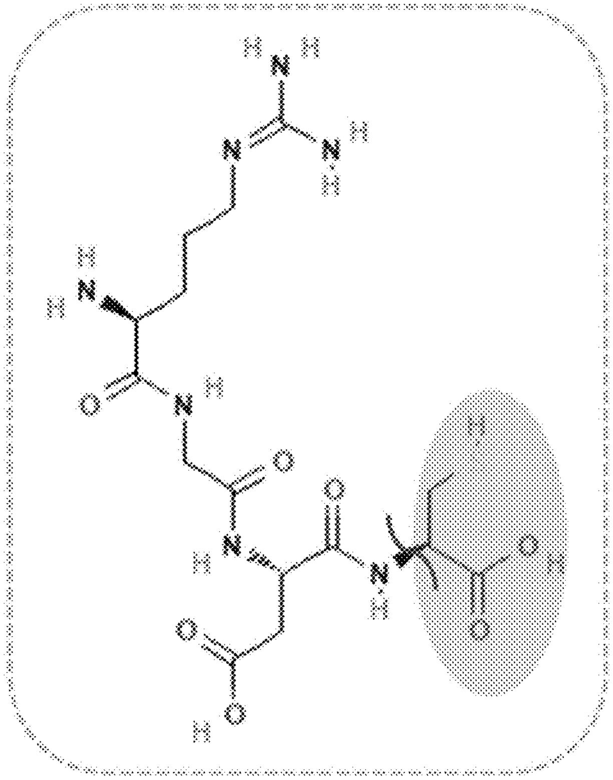
FIG. 6 shows the structure of RGDC ligand, wherein a C—N bond is broken so that a portion of the ligand stays attached to the $Au_{16}$ core.

Mass spectrometry of water-soluble clusters remains challenging due to the ease of the fragmentation as well as complex isotope patterns. Hydrophilic ligands with terminal carboxylic acid usually exist in carboxylate form at pH >5. This high charge density of the ligands results in significant fragmentation after ionization. Mass spectrometry cannot be solely used to indicate the purity of the clusters and should be used in complement with other data such as fluorescence EEM spectra, to better explain the clusters purity. Using the softest ionization conditions (voltage, gas flow) possible in positive ion mode in ESI-MS, a signal was obtained and the assignment of $Au_{16}(RGDC)_{14}$ was made (FIG. 5). The most intense peak at 2130.37 m/z is well matched with $Au_{16}(SC_3H_6)_{14}Na_3H_2$ (z=+2). As a result of ligand fragmentation, a C—N bond is broken so that only a portion of the ligand stays attached to the $Au_{16}$ core (FIG. 6).

The absorbance of the $Au_{16}(RGDC)_{14}$ clusters was found to be slightly blue shifted and the fluorescence intensity decreased at acidic (pH 4) versus basic or neutral pH. Ligands play an important role in the electronic properties and excited state behaviour of thiolated clusters. Furthermore, it is possible that the clusters adopt different conformations based on the protonation state of the ligands which then affect the excited state dynamic and fluorescent intensity.

Figure 7:
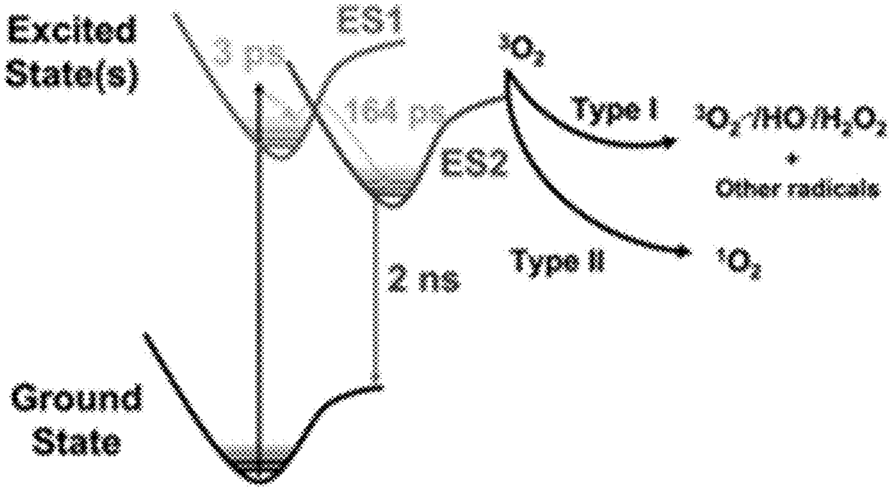
FIG. 7 is a diagram of the electronic excitation and excited state dynamics involved in the relaxation of $Au_{16}(RGDC)_{14}$ clusters and ROS generation pathways.

To probe the excited state behaviour of clusters, femtosecond transient absorbance spectroscopy, also called pump-probe spectroscopy, was used. The technique provides valuable information in assessing excited state lifetimes and properties related to activity as a photosensitizer. It uses two laser pulses: the first, the pump, is used to excite the sample at a single wavelength and the other, the probe (a white light pulse), is delayed in time and probes changes in absorbance of the sample in the excited state. The difference spectrum (excited state absorbance minus ground state absorbance) is recorded in time, allowing for dynamics of the excited state and relaxation to the ground state to be monitored. Herein, an aqueous solution (pH=7) of $Au_{16}(RGDC)_{14}$ clusters was excited with 250 fs FWHM pump centred at 340 nm, and the transient absorption was recorded up to 5 ns after excitation. The results and measured relaxation rates (lifetimes) suggest that the clusters exhibit three relaxation components; (1) thermalization of hot electrons, (2) dynamics on the ~1000 ps timescale that are attributed to formation of a reactive/emissive excited state, and (3) nanosecond to microsecond emission or reactivity from the lowest lying excited state. A Jablonski diagram is shown in FIG. 7 to illustrate the excited state behaviour of the clusters and possible reaction pathways with oxygen.

Figure 8A:
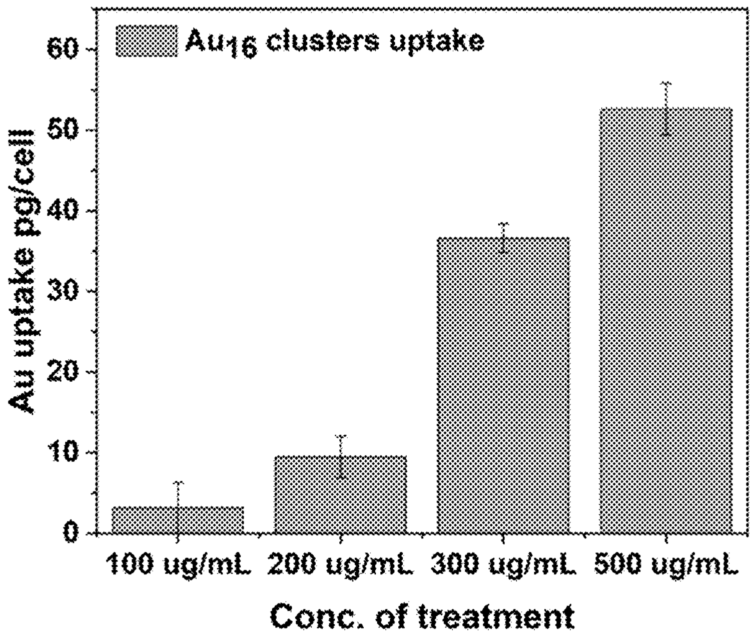
FIGS. 8A and 8B are plots showing uptake and viability, respectively, of KB cells incubated with $Au_{16}(RGDC)_{14}$ clusters following a 20-minute irradiation using a 500 nm LED, wherein viability measurements taken 48 hours after completion of irradiation.
Figure 8B:
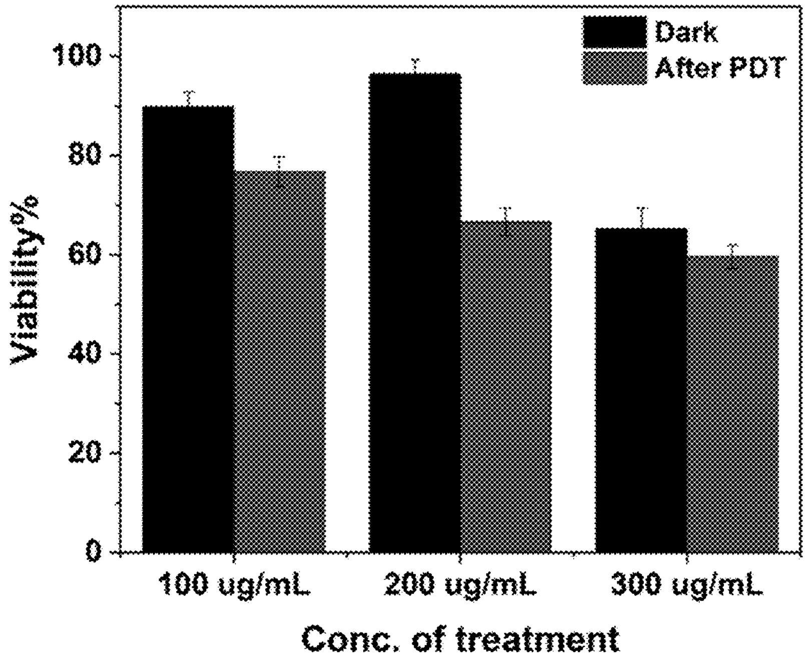

As the $Au_{16}(RGDC)_{14}$ clusters were found to be stable at physiological pH, the cellular uptake and photosensitizer ability of the clusters was assessed on KB cells (a commonly used subset of HeLa, or cervical adenocarcinoma cells) (FIGS. 8A and 8B). KB cells were seeded at 40,000 cells per well in 24-well plates and cultured in RPMI 1640 cell culture media with 10% fetal bovine serum (FBS) at 37° C. under a humidified atmosphere containing 5% $CO_2$ for 48 hours. The $Au_{16}(RGDC)_{14}$ clusters were then added to the cells at concentrations of 100, 200, 300, and 500 μg/mL, in triplicate, and incubated for 24 hours. On the same plate, five wells were left untreated from clusters, containing just KB cells in cell media to be used as a control. After 24 hours of incubation with the clusters, cell viability was determined by calculating the mean viability of cells from the control wells and comparing it to the mean viability of non-control cells using an Alamar blue assay.

The photosensitizer ability of the clusters was then assessed using the same cell culturing and plating method used for cell viability. This time, KB cells were dosed at 100, 200, and 300 μg/mL of the $Au_{16}(RGDC)_{14}$ clusters in triplicate. Those were the concentrations of the clusters which had the highest viability in cell dark toxicity studies. After 24 hours of incubation with the clusters, the cell medium of each well was replaced with a fresh medium. The plates were then irradiated using visible light (500 nm LED light for 20 minutes (40 J/cm$^2$)), and were incubated for an additional 48 hours before assessing if damaged cells were able to recover and survive. The cells were counted with an Alamar blue assay and the viability rate for each well was then calculated by comparing to non-treatment (no clusters) control cells. The clusters were able to induce significant cell death after irradiation at concentration of 200 μg/mL (up to 30%, FIG. 7B). Furthermore, gold clusters exhibit two photon cross sections and perform two-photon PDT as well. Given the potent PDT performance of $Au_{16}(RGDC)_{14}$ clusters, investigations were carried out to determine whether Type I or Type II ROS generation was responsible for the effect.

Figure 9A:
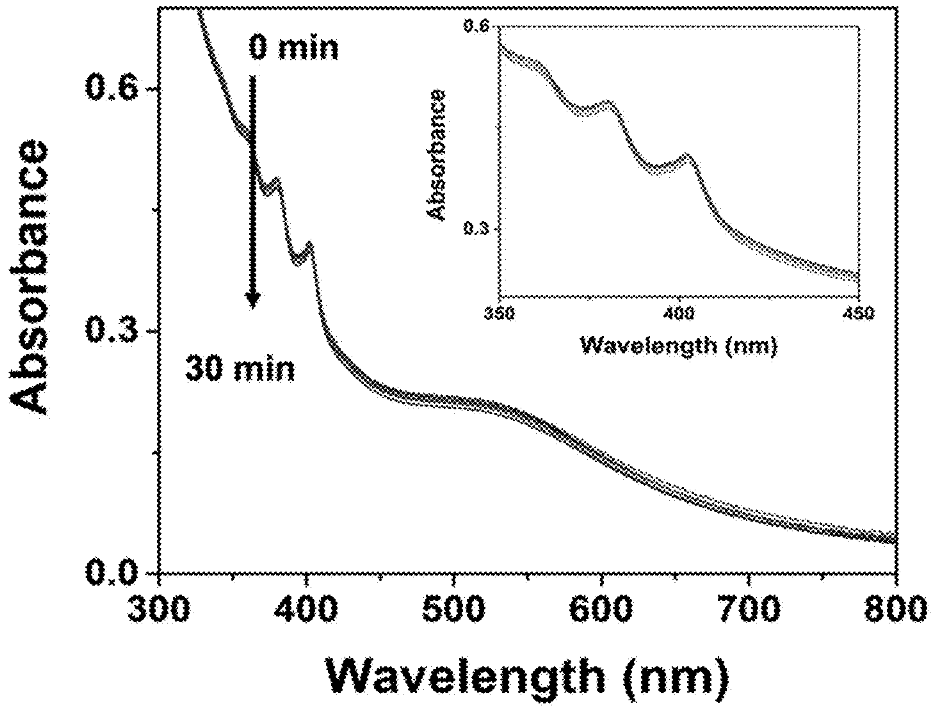
FIGS. 9A and 9B are plots of absorbance spectra of $Au_{16}(RGDC)_{14}$ clusters and MB in ABDA aqueous solution, respectively.
Figure 9B:
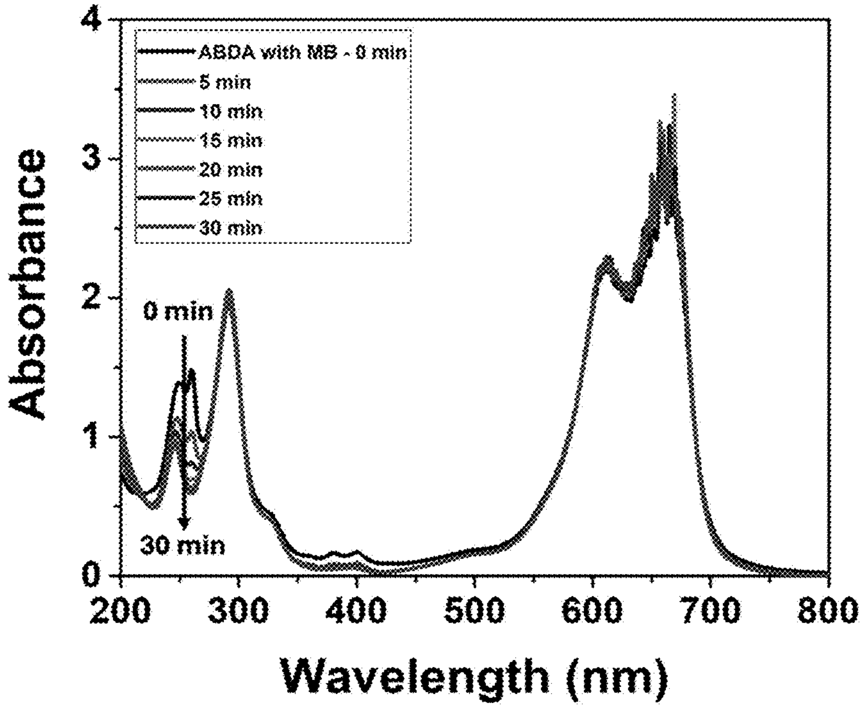

The production of $^1O_2$ by $Au_{16}(RGDC)_{14}$ clusters was assessed using 9,10-anthracenediyl-bis(methylene)dimalonic acid (ABDA), which is soluble in water and acts as a specific probe for the detection of $^1O_2$. ABDA undergoes oxidation in the presence of $^1O_2$ to form the endoperoxide $ABDAO_2$, quantitatively reducing the absorbance at of the ABDA at 350-400 nm. Methylene blue (MB) was used as a positive control, which has a QY of photochemical generation of $^1O_2$ of 0.52. Two solutions were prepared using equimolar concentrations of the ABDA in water. For the first solution, 50 μL of ABDA stock solution (0.15 mg/ml) was added to the clusters with a total solution volume of 2.6 mL, and the absorbance of the clusters and the probe were adjusted to 0.2 at 520 nm (the excitation wavelength). To the other solution, 50 μL of the ABDA was added to the 2.6 mL MB solution, where the absorbance of the MB and the probe were matched to 0.2 at 520 nm. Each sample was irradiated using 520 nm LED light in 5 m intervals up to 30 minutes and absorbance spectra were acquired at each interval. Although an absorbance decrease was observed for the MB, indicating that $^1O_2$ was generated, no specific change occurred when using $Au_{16}(RGDC)_{14}$ clusters (FIGS. 9A and 9B), suggesting that the clusters do not efficiently generate $^1O_2$.

Although the $Au_{16}(RGDC)_{14}$ clusters do not appear to be potent Type II photosensitizers, the PDT results with KB cells suggest that they can generate other reactive species (e.g., Type 1). To assess Type I ROS generation of the clusters, 2,7-dichlorodihydrofluorescein (DCFH) was used where non-fluorescence DCFH is oxidized by oxygen centered radicals and form dichlorofluorescein (DCF), which is emissive at 525 nm. This probe was chosen since it is specific to Type I ROS such as $H_2O_2$, $HO^•$, and $ROO^•$. An ethanol solution containing 250 μL of DCFH (1 mM) was added to a 1 mL sodium hydroxide solution (0.01 mM) and diluted with 5 mL of PBS buffer to hydrolyze for 30 minutes in the dark. Then 200 μL of $Au_{16}(RGDC)_{14}$ clusters were added to 1 mL of DCFH solution, followed by irradiation with a Xe lamp (100 $mWcm^2$) for 1 min intervals.

Figure 10:
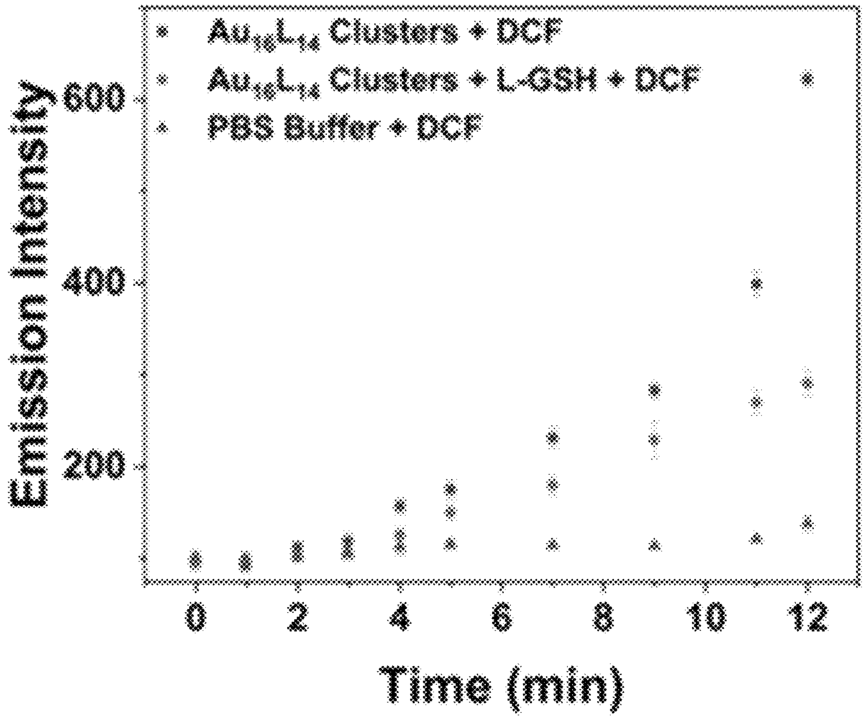
FIG. 10 is a plot of fluorescent intensity of DCF at 525 nm with Xe lamp irradiation for treatment of $Au_{16}(RGDC)_{14}$ nanoclusters, PBS blank, and clusters with L-glutathione at 488 nm excitation wavelength.

The fluorescence intensity of DCFH-containing solution of the clusters increased upon irradiation with a Xe lamp for 12 min, indicating generation of ROS (FIG. 10). Without clusters there is almost no fluorescence signal for DCFH in phosphate buffered saline (PBS) solution. The fluorescence intensity of the probe exhibited a non-linear increasing in the presence of $Au_{16}(RGDC)_{14}$ and did not reach a plateau over 12 minutes of irradiation. Since the excited state of the clusters transfers electrons to generate Type I ROS, the clusters themselves become oxidized in the process. The oxidized clusters are postulated to exhibit a higher rate of ROS production. To test this hypothesis, reduced L-glutathione (L-GSH) was added to the solution of the clusters and the probe. L-GSH is the most abundant peptide in the body and acts as an antioxidant, and as such can donate an electron thus preventing the formation of oxidized clusters. The DCF fluorescence intensity linearly increased over 12 m of irradiation when L-GSH was added, suggesting that $Au_{16}(RGDC)_{14}$ clusters are stable as a photosensitizer with a sacrificial antioxidant present, that they effectively produce Type I ROS, and that the process can be photocatalytic under cell conditions (i.e., in vivo) with L-GSH present. This data also illustrates that the generation of ROS is highly dependent on the excited-state reactivity of the clusters and their exact composition. It is important to note that Type I PDT can be advantageous over Type 11 PDT by reacting with substrates other than oxygen, especially in hypoxic cell environments common to cancerous tumours.

Overall the results suggest that the $Au_{16}(RGDC)_{14}$ nanocluster functions as photosensitizer in cells and tissues and thus has utility in applications such as, but not limited to, biomedical applications and photocatalysis. For example, the nanoclusters may be useful in photodynamic therapy (PDT), which may be used in treating diseases such as certain cancers. As an example, a method for providing photodynamic therapy to a subject may include providing $Au_{16}(RGDC)_{14}$ nanoclusters in a suitable vehicle to the subject, wherein cells of the subject uptake the nanoclusters, and exposing the cells that uptake the nanoclusters to irradiation with light, wherein cell death is induced in at least a portion of the cells that uptake the $Au_{16}(RGDC)_{14}$ nanoclusters. In some embodiments the at least a portion of the cells that uptake the Au16(RGDC)14 nanoclusters are cancer cells, and cell death is induced in at least a portion of the cancer cells that uptake the Au16(RGDC)14 nanoclusters.

All cited publications are incorporated herein by reference in their entirety.

EQUIVALENTS

It will be appreciated that modifications may be made to the embodiments described herein without departing from the scope of the invention. Accordingly, the invention should not be limited by the specific embodiments set forth, but should be given the broadest interpretation consistent with the teachings of the description as a whole.

REFERENCES

1. Sych, T. S.; Reveguk, Z. V.; Pomogaev, V. A.; Buglak, A. A.; Reveguk, A. A.; Ramazanov, R. R.; Romanov, N. M.; Chikhirzhina, E. V.; Polyanichko, A. M.; Kononov, A. I., Fluorescent Silver Clusters on Protein Templates: Understanding Their Structure. The Journal of Physical Chemistry C 2018, 122 (51), 29549-29558.
2. Tang, L.; Zeng, X. D.; Zhou, H.; Gui, C. H.; Luo, Q. L.; Zhou, W. Y.; Wu, J.; Li, Q. Q.; Li, Y.; Xiao, Y. L., Theranostic Gold Nanoclusters for NIR-II Imaging and Photodynamic Therapy. CHEMICAL RESEARCH IN CHINESE UNIVERSITIES 2021, 37 (4), 934-942.
3. Zhang, Y.; Zhang, C.; Xu, C.; Wang, X.; Liu, C.; Waterhouse, G. I. N.; Wang, Y.; Yin, H., Ultrasmall Au nanoclusters for biomedical and biosensing applications: A mini-review. Talanta 2019, 200, 432-442.
4. Ramsay, H. S.; Silverman, M. M.; Simon, D.; Oleschuk, R. D.; Stamplecoskie, K. G., Light activated synthesis of the atomically precise fluorescent silver cluster Ag18 (Capt)14. Nanoscale 2019, 11 (43), 20522-20526.
5. Stamplecoskie, K. G.; Chen, Y.-S.; Kamat, P. V., Excited-State Behavior of Luminescent Glutathione-Protected Gold Clusters. The Journal of Physical Chemistry C 2014, 118 (2), 1370-1376.
6. Yousefalizadeh, G.; Stamplecoskie, K. G., Norrish type I photochemistry as a powerful tool in the isolation of thiol protected Au25SR18 clusters. Journal of Photochemistry and Photobiology A: Chemistry 2018, 353, 251-254.22. Conway, C. L.; Walker, I.; Bell, A.; Roberts, D. J.; Brown, S. B.; Vernon, D. I., In vivo and in vitro characterisation of a protoporphyrin IX-cyclic RGD peptide conjugate for use in photodynamic therapy. Photochem Photobiol Sci 2008, 7 (3), 290-8.
7. Kawasaki, H.; Kumar, S.; Li, G.; Zeng, C.; Kauffman, D. R.; Yoshimoto, J.; Iwasaki, Y.; Jin, R., Generation of Singlet Oxygen by Photoexcited Au25(SR)18 Clusters. Chemistry of Materials 2014, 26 (9), 2777-2788.
8. Conway, C. L.; Walker, I.; Bell, A.; Roberts, D. J.; Brown, S. B.; Vernon, D. I., In vivo and in vitro characterisation of a protoporphyrin IX-cyclic RGD peptide conjugate for use in photodynamic therapy. Photochem Photobiol Sci 2008, 7 (3), 290-8.
9. Yin, Y.; Zhu, W.-W.; Guo, L.-P.; Yang, R.; Li, X.-S.; Jiang, Y., RGDC Functionalized Titanium Dioxide Nanoparticles Induce Less Damage to Plasmid DNA but Higher Cytotoxicity to HeLa Cells. The Journal of Physical Chemistry B 2013, 117 (1), 125-131.
10. He, L.; Huang, Y.; Chang, Y.; You, Y.; Hu, H.; Leong, K. W.; Chen, T., A highly selective dual-therapeutic nanosystem for simultaneous anticancer and antiangiogenesis therapy. Journal of Materials Chemistry B 2017, 5 (41), 8228-8237.
11. Wan, Z.; Zhang, P.; Lv, L.; Zhou, Y., NIR light-assisted phototherapies for bone-related diseases and bone tissue regeneration: A systematic review. Theranostics 2020, 10 (25), 11837-11861.
12. Li, R.; Zhou, Y.; Liu, Y.; Jiang, X.; Zeng, W.; Gong, Z.; Zheng, G.; Sun, D.; Dai, Z., Asymmetric, amphiphilic RGD conjugated phthalocyanine for targeted photodynamic therapy of triple negative breast cancer. Signal Transduction and Targeted Therapy 2022, 7 (1), 64.

The invention claimed is:

1. A gold nanocluster of the formula $Au_{16}(RGDC)_{14}$; wherein RGDC is arginine-glycine-aspartic acid-cysteine.

2. A method for photodynamic therapy in a subject in need thereof, comprising administering the gold nanocluster of claim 1 to the subject and irradiating the subject with light.

3. The method of claim 2, wherein the subject has cancer.

4. The method of claim 2, wherein the gold nanocluster is administered in an amount of about 500 μg/mL.

5. The method of claim 2, wherein the light is visible light.

6. A method for synthesizing the gold nanocluster of claim 1 comprising the steps of:

a) reacting 3 mM aqueous solution of $HAuCl_4$ with 9 mM aqueous solution of RGDC;

b) adding 3 mM aqueous solution of 2-hydroxy-4'-(2-hydroxyethoxy)-2-methylpropiophenone to the reaction of step a) and adjusting the pH of the reaction to 10;

c) irradiating the reaction at about 360 nm; and d) purifying the gold nanocluster by centrifugation.

7. The method of claim 6, comprising centrifuging using centrifugal filters with a cut-off of about 3 kDa.

8. The method of claim 6, comprising centrifuging to remove unwanted photoproducts emitting at about 420 nm.

9. The method of claim 6, comprising monitoring absorbance and excitation-emission matrix (EEM) spectra of the product during the irradiating.

10. The method of claim 9, comprising performing parallel factor (PARAFAC) analysis on EEM spectra to determine emissive components and their relative contributions to the emission of the product.

11. The method of claim 10, comprising removing Rayleigh scattering from each EEM spectra prior to PARAFAC analysis.

12. The method of claim 10, comprising determining a score value of at least one component of a model of the product for successive EEM spectra, determining a plateau of the score value of the at least one component, and stopping the reaction by stopping the UVA irradiation when the plateau in the score value of the at least one component is reached.

* * * * *